United States Patent

Hausheer et al.

[11] Patent Number: 6,040,330
[45] Date of Patent: Mar. 21, 2000

[54] PHARMACEUTICAL FORMULATIONS OF TAXANES

[75] Inventors: Fredrick H. Hausheer, Boerne; Dhanabalan Murali; Peddaiahgari Seetharamulu, both of San Antonio, all of Tex.

[73] Assignee: BioNumerik Pharmaceuticals, Inc., San Antonio, Tex.

[21] Appl. No.: 09/226,968

[22] Filed: Jan. 8, 1999

[51] Int. Cl.[7] .................................................. A61K 31/40

[52] U.S. Cl. ................... 514/408; 514/408; 514/283; 514/423; 514/549; 514/449; 435/108; 424/450; 424/490; 548/335.1

[58] Field of Search ...................... 514/283, 423, 514/449, 408, 549; 424/450, 455, 490, 489; 528/421; 549/511

[56] References Cited

U.S. PATENT DOCUMENTS

| 5,399,363 | 3/1995 | Liversidge et al. | 424/490 |
|---|---|---|---|
| 5,498,421 | 3/1996 | Grinstaff et al. | 424/450 |
| 5,614,549 | 3/1997 | Greenwald et al. | 514/449 |
| 5,859,023 | 1/1999 | Hausheer et al. | 514/283 |

FOREIGN PATENT DOCUMENTS

| 703778 | 6/1997 | European Pat. Off. | A61K 9/127 |

*Primary Examiner*—Keith D. MacMillan
*Assistant Examiner*—Vickie Kim
*Attorney, Agent, or Firm*—Thomas J. Dodd

[57] ABSTRACT

A pharmaceutical formulation of a taxane antineoplastic agent, particularly paclitaxel or docetaxel or a pharmaceutically acceptable salt thereof, and N-methylpyrrolidin-2-one (NMP). The formulation may include other excipients and/or diluents, and is suitable for administration to patients with cancer.

8 Claims, No Drawings

PHARMACEUTICAL FORMULATIONS OF TAXANES

FIELD OF THE INVENTION

This invention relates to pharmaceutical formulations of taxanes, particularly the antitumor drugs Paclitaxel (Taxol) and Docetaxel (Taxotere), or derivatives thereof, and N-methylpyrrolidin-2-one (NMP).

BACKGROUND OF THE INVENTION

1. Background of Paclitaxel and Docetaxel

Taxanes, in particular, the two currently available drugs, Paclitaxel and Docetaxel, are potent antineoplastic agents. Taxanes are derived naturally or semi-synthetically from the bark or needles of certain yews. Paclitaxel was discovered in the late 1970s, and was found to be an effective antineoplastic agent with a mechanism of action different from existing chemotherapeutic agents.

In particular, Paclitaxel, Docetaxel and other taxanes exert cytotoxic effects by enhancing the polymerization of tubulin, which is an essential protein in the formation of spindle microtubules. The result is the formation of very stable, nonfunctional tubules, which inhibits cell replication and leads to neoplasm cell death. Taxanes are recognized as effective agents in the treatment of many solid tumors which are refractory to other antineoplastic agents.

Paclitaxel has a complex structure and is shown below as Formula I:

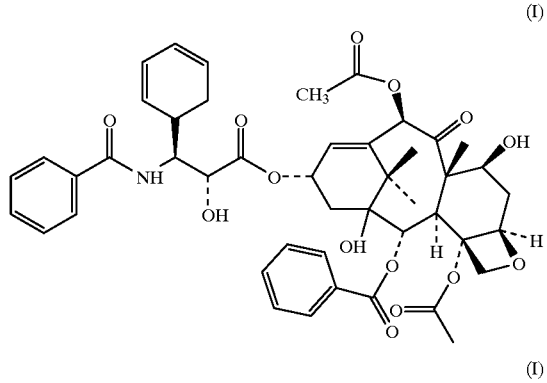

(I)

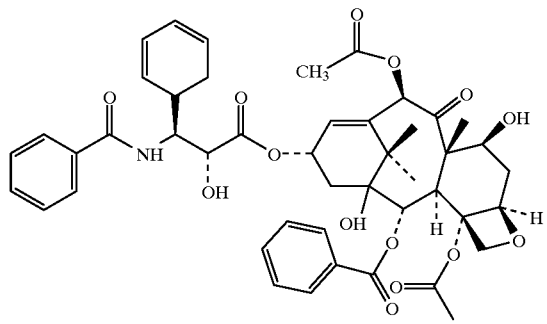

(I)

Paclitaxel is very poorly water soluble (less than 10 μg/mL), and as a result, cannot be practically formulated with water for IV administration. Currently, Paclitaxel is formulated for IV administration to patients with cancer in a solution with polyoxyethylated castor oil (Polyoxyl 35 or Cremaphor®) as the primary solvent. High concentrations of ethanol are employed as co-solvents. One of the major difficulties in the administration of Paclitaxel is the occurrence of hypersensitivity reactions. These reactions, which include severe skin rashes, hives, flushing, dyspnea, tachycardia, and others, may be attributed at least in part to the high concentrations of alcohol and polyoxyl 35 used as solvents in the formulation.

Docetaxel is an analogue of Paclitaxel, and was recently approved for administration to patients with cancer by the United States Food & Drug Administration. Docetaxel has the following structure:

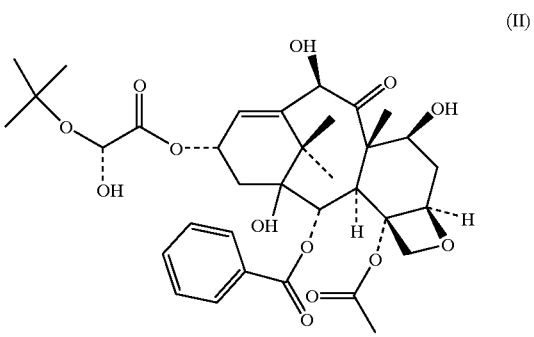

(II)

Like Paclitaxel, Docetaxel is very poorly soluble in water. The current most preferred solvent used to dissolve Docetaxel is polysorbate 80 (Tween 80). Like Polyoxyl 35, polysorbate often causes hypersensitivity reactions in patients. Further, polysorbate cannot be used with PVC delivery apparatus, because of its tendency to leech diethylhexyl phthalate, which is highly toxic.

Due to the relatively high viscosity of Cremaphor, co-solvents must be employed to allow for intravenous infusion of the formulation to the patient. Some commonly employed co-solvents include various lower alcohols, vegetable and other oils, and combinations of other organic and inorganic solvents. Other pharmaceutical excipients are also employed in making formulations of these drugs. Currently, only intravenous formulations of paclitaxel or docetaxel are available for administration to patients.

2. N-Methylpyrrolidone

N-methylpyrrolidin-2-one, also referred to as N-methylpyrrolidone, 1-methyl-2-pyrrolidone, NMP, and other like names, is a common industrial solvent. NMP has also been used in pharmaceutical formulations as an excipient to enhance the skin penetration of topically applied agents. NMP is a slow evaporating, highly polar, aprotic, general purpose solvent which is fully miscible with water and most organic solvents. The many uses of NMP are catalogued in the BASF brochure entitled N-Methylpyrrolidone (NMP), attached to the Information Disclosure Sheet (IDS). NMP has also been used in the preparation of pharmaceutical compounds as a solvent for various pharmaceuticals, namely Etoposide, Tetracycline, Doxycycline, Teniposide, Chlortetracycline, Camptothecins and other poorly water soluble pharmaceutical compounds. Prior patents regarding the use of NMP as such are identified in and attached to the Information Disclosure Sheet.

SUMMARY OF THE INVENTION

The pharmaceutical formulations of this invention include as principal ingredients an effective amount of a taxane (the active ingredient), and an amount of NMP sufficient to dissolve all of the active ingredient. The formulation may also include other pharmaceutical excipients commonly found in formulations suitable for intravenous administration.

Accordingly, it is an object of this invention to provide for a novel pharmaceutical formulation which includes as one of the active ingredients, an effective amount of a taxane.

Another object of this invention is to provide for an intravenous formulation of a taxane which is easy and safe to administer.

Other objects of this invention will become apparent upon reading the following specification.

DESCRIPTION OF THE PREFERRED EMBODIMENTS

The preferred embodiments herein described are not intended to be exhaustive or to limit the invention to the precise form disclosed. They are chosen and described to explain the principles of the invention and its application and practical use to enable others skilled in the art to follow its teachings.

The pharmaceutical formulations of this invention each include two basic ingredients: 1) a taxane (the active ingredient); and 2) a primary solvent, NMP, in sufficient volume to dissolve all of the active ingredient. The formulation is packaged for intravenous administration to a patient in need of treatment for cancer, the approved use of the active ingredient.

The formulation may also include quantities of various other excipients as desired. Excipients are used for a number of purposes in formulating pharmaceuticals, namely as surfactants, thickeners/thinners, pH controllers, stabilizers, etc. Examples of some typical excipients, and their general usage and function are described below.

TABLE 1

| | |
|---|---|
| Polyethylene Glycol (PEG 200, PEG 300, PEG 400, etc.) | Thickening Agent/Solvent |
| Organic and Inorganic Acids | pH Lowering Agents |
| Organic and Inorganic Bases | pH Raising Agents |
| Epoxylated Castor Oil (Cremaphor) | Surfactant |
| Alcohols (Ethanol or Benzyl Alcohol preferred) | Co-solvents |
| Poloxamers and/or polysorbates (407, PF-127, Tween 80, etc.) | Surfactant |
| Glycerin | Co-solvent |
| Dimethylisosorbide | Co-solvent |
| Dimethylacetamide | Co-solvent |
| Glycerin | Co-solvent |
| Water | Diluent |
| Saline | Diluent |

All diluents, carriers and excipients used in the formulation are pharmaceutically acceptable compounds.

The formulation is preferably prepared in the following manner. First, the active ingredient is completely dissolved in the primnary solvent, in this invention, NMP. Second, the other additives and excipients are added, either individually or in combination to complete the formulation. The formulation is then typically packaged and shipped.

Finally, the completed formulation is diluted with water, or a common parenteral delivery vehicle, such as a saline solution (0.1%–0.9% NaCl), Lactated Ringer's Solution, 5% Dextrose USP, or the like. The final dilution is usually performed at the hospital or treatment center just prior to administration to the patient.

Preferred pharmaceutical formulations of taxanes include a pharmaceutically effective amount of the taxane dissolved in an amount of NMP sufficient to dissolve all of the taxane.

The current recommended dosage range for Paclitaxel is between 100–250 mg/m$^2$ and the current recommended dosage for Docetaxel ranges from 50–150 mg/m$^2$. Since a typical adult patient's body surface area is between 1.5–2.0 m$^2$, a preferred total dose will range from 150–500 mg of Paclitaxel, and from 75–300 mg of Docetaxel. When the patient's body surface area is outside these ranges, dosage is adjusted to account for this variability.

The maximum solubility of Paclitaxel and Docetaxel in NMP has been determined to be approximately 40 mg/mL. Since an amount of NMP sufficient to dissolve all of the taxane is preferred, preferred formulations will include at least from 4–13 mL of NMP for Paclitaxel, and from 2–8 mL of NMP for Docetaxel. These volumes will often be higher, to ensure complete dissolution of the taxane in the primary solvent.

The preferred formulations are prepared by adding the effective amount of the taxane to a volume of NMP predetermined to be sufficient to dissolve all of the taxane. To this NEAT formulation are added the desired excipients. The concentrated formulation is then packaged and distributed. The concentrated formulation is diluted in a conventional parenteral delivery carrier, supra, just prior to administration to the patient. A preferred taxane/NMP formulation is shown below in Table 2.

TABLE 2

| Ingredient | Specific Compound | Amount |
|---|---|---|
| Active Ingredient | Paclitaxel | 200 mg |
| Solvent | NMP | 10 mL |
| Diluent | Ethanol | 50–100 mL |
| Surfactant | Cremaphor | 10–500 mL |
| pH Adjuster | Citric Acid | 1–5 mL |
| Excipient | PEG 200 | 10–500 mL |
| Surfactant | Tween 80 | 10–500 mL |

After the formulation has been packaged, it is administered to a patient in accordance with the patient's treatment regimen, taking into account the recommended dosage and rate schedules prescribed by the attending physician.

It is understood that the above description is presented for illustrative purposes only, and should in no way be construed as limiting the invention to the precise details above given.

What is claimed is:

1. A pharmaceutical formulation comprising a taxane and N-methylpyrrolidin-2-one.

2. The pharmaceutical formulation of claim 1 wherein said taxane is Paclitaxel.

3. The pharmaceutical formulation of claim 1 wherein said taxane is Docetaxel.

4. The pharmaceutical formulation of claim 1 wherein said formulation also includes a lower alcohol.

5. The pharmaceutical formulation of claim 1 wherein said formulation further includes a non-ionic surfactant.

6. A pharmaceutical formulation comprising Paclitaxel or Docetaxel, or a pharmaceutically acceptable salt thereof, and N-methylpyrrolidin-2-one.

7. The pharmaceutical formulation of claim 6 wherein said formulation further includes a lower alcohol.

8. The pharmaceutical formulation of claim 6 wherein said formulation further includes a non-ionic surfactant.

* * * * *